(12) United States Patent
Alt et al.

(10) Patent No.: US 6,767,360 B1
(45) Date of Patent: Jul. 27, 2004

(54) VASCULAR STENT WITH COMPOSITE STRUCTURE FOR MAGNETIC REASONANCE IMAGING CAPABILITIES

(75) Inventors: Eckhard Alt, Ottobrunn (DE); Torsten Scheuermann, Munich (DE); Michael Kühling, Munich (DE)

(73) Assignee: Inflow Dynamics Inc., Springfield, VA (US)

(*) Notice: Subject to any disclaimer, the term of this patent is extended or adjusted under 35 U.S.C. 154(b) by 0 days.

(21) Appl. No.: 09/779,204

(22) Filed: Feb. 8, 2001

(51) Int. Cl.[7] .................................................. A61F 2/06
(52) U.S. Cl. ...................... 623/1.15; 623/1.27; 623/1.44
(58) Field of Search ............................. 623/1.15, 1.23, 623/1.27, 1.32, 1.34, 1.44

(56) References Cited

U.S. PATENT DOCUMENTS

| | | | |
|---|---|---|---|
| 5,651,047 A | | 7/1997 | Moorman et al. |
| 5,667,523 A | * | 9/1997 | Bynon et al. ............... 606/198 |
| 5,824,045 A | * | 10/1998 | Alt ................................ 623/1 |
| 6,099,561 A | * | 8/2000 | Alt ............................ 623/1.44 |
| 6,171,240 B1 | | 1/2001 | Young et al. |
| 6,231,516 B1 | | 5/2001 | Keilman et al. |
| 6,238,491 B1 | * | 5/2001 | Davidson et al. ........... 148/237 |
| 6,264,611 B1 | | 7/2001 | Ishikawa et al. |
| 6,280,385 B1 | | 8/2001 | Melzer et al. |
| 6,332,089 B1 | | 12/2001 | Acker et al. |

FOREIGN PATENT DOCUMENTS

| | | |
|---|---|---|
| WO | WO 92/12681 | 8/1992 |
| WO | WO 97/29709 | 8/1997 |
| WO | WO 00/30534 | 6/2000 |
| WO | WO 01/56469 A2 | 8/2001 |
| WO | WO 01/73461 A2 | 10/2001 |
| WO | WO 01/74241 A1 | 10/2001 |
| WO | WO 02/30331 A1 | 4/2002 |
| WO | WO 02/40088 A2 | 5/2002 |
| WO | WO 02/084316 A1 | 10/2002 |

OTHER PUBLICATIONS

Avery, "Why does't stainless steel rust?", Aug. 2001, Scientific American.*

* cited by examiner

*Primary Examiner*—Bruce Snow
(74) *Attorney, Agent, or Firm*—Fish & Richardson P.C.

(57) ABSTRACT

A stent is adapted to be implanted in a duct of a human body to maintain an open lumen at the implant site, and to allow viewing body tissue and fluids by magnetic resonance imaging (MRI) energy applied external to the body. The stent constitutes a metal scaffold. An electrical circuit resonant at the resonance frequency of the MRI energy is fabricated integral with the scaffold structure of the stent to promote viewing body properties within the lumen of the stent.

20 Claims, 3 Drawing Sheets

VASCULAR STENT WITH COMPOSITE STRUCTURE FOR MAGNETIC REASONANCE IMAGING CAPABILITIES

CROSS-REFERENCE TO RELATED APPLICATION

The prestent application is related to U.S. application Ser. No. 09/663,896, assigned to the same assignee as the prestent application.

BACKGROUND OF THE INVENTION

Interventional cardiology, interventional angiology and other interventional techniques in cardiovascular and other vessels, ducts and channels of the human body have demonstrated marked success in recent years. Studies of interventions in the treatment of acute myocardial infarction (MI), for example, indicate the effectiveness of primary angioplasty. Implantation of coronary stents has improved the outcome of such interventional treatment. For example, these results are described in an article in the Journal of American College of Cardiology 2000, 36: 1194–1201.

Stents are being implanted in increasing numbers throughout the world to treat heart and cardiovascular disease, and are also coming into greater use outside strictly the field of cardiology. For example, other vascular interventions utilizing stents which are proving to be of equal importance to use in cardiology include stenting of the carotid, iliac, renal, and femoral arteries. Moreover, vascular intervention with stents in cerebral circulation is exhibiting quite promising results, especially in patients suffering acute stroke.

Stents are implanted in vessels, ducts or channels of the human body to act as a scaffolding to maintain the patency of the vessel, duct or channel lumen. A drawback of stenting is the body's natural defensive reaction to the implant of a foreign object. In many patients, the reaction is characterized by a traumatic proliferation of tissue as intimal hyperplasia at the implant site, and, where the stent is implanted in a blood vessel such as a coronary artery, formation of thrombi which become attached to the stent. Each of these adverse effects contributes to restenosis—a re-narrowing of the vessel lumen—to compromise the improvements that resulted from the initial re-opening of the lumen by implanting the stent. Consequently, a great number of stent implant patients must undergo another angiogram, on average about six months after the original implant procedure, to determine the status of tissue proliferation and thrombosis in the affected lumen. If re-narrowing has occurred, one or more additional procedures are required to stem or reverse its advancement.

For virtually all stent implant patients it is desirable to examine and analyze the patency of the vessel lumen and the extent of tissue growth within the lumen of the stent, and to measure blood flow therethrough, from time to time as part of the patient's routine post-procedure examinations. Current techniques employed to analyze patency of the lumen following a stent implant procedure are more or less invasive.

Among these techniques is vascular puncture, which, despite a relatively low complication rate, poses inherent risks as well as discomfort of the patient, such as a need for compression of the puncture site. Use of iodine containing contrast dye also prestents the possibility of negative implication such as renal failure, especially in patients with diabetes. If contrast dyes are applied to a cerebral perfusion, tissue damage may cause neurological seizures and temporary cerebral dysfunction. Therefore, it is advantageous to determine the vascular status and the functional and morphological capacity of the vascular bed by less or non-invasive methods, including methods not requiring application of iodine containing contrast dye.

Fluoroscopic techniques are an unsuitable substitute or alternative for the invasive methods because the metal stent itself causes blockage of the x-rays. Although visualization of the stent is achieved by its fluoroscopic portrayal as a shadow during the original implant procedure, the stent's very presence defeats subsequent examination of the interior condition of the stent and the vessel lumen at the implant site by means of fluoroscopy following the implant procedure, without the use of contrast dye applied intravascularly.

Magnetic resonance imaging (MRI) can be used to visualize internal features of the body if there is no magnetic resonance distortion. MRI has an excellent capability to visualize the vascular bed, with particularly accurate imaging of the vascular structure being feasible following the application of gadolinium, a contrast dye which enhances the magnetic properties of the blood and which stays within the vascular circulation. This has special implications for the perfusion in vessels which are in a stable and resting state, especially iliac, femoral, carotid, and cerebral perfusion. On occasion of acute cerebrovascular stroke, the diagnosis of a blocked artery can be achieved quickly, within minutes, by means of an MRI technique following the intravenous injection of 30 milliliters (ml) of gadolinium.

Imaging procedures using MRI without need for contrast dye are emerging in the practice. But a current considerable factor weighing against the use of magnetic resonance imaging techniques to visualize implanted stents composed of ferromagnetic or electrically conductive materials is the inhibiting effect of such materials. These materials cause sufficient distortion of the magnetic resonance field to preclude imaging the interior of the stent. This effect is attributable to their Faradaic physical properties in relation to the electromagnetic energy applied during the MRI process.

It is a primary aim of the prestent invention to provide a stent structure and method that enables imaging and visualization of the inner lumen of an implanted stent by means of an MRI technique without need for X-ray or contrast dye application. A related aim is to enable analysis and evaluation of the degree of tissue proliferation and thrombotic attachment within the stent, and thereby, calculation of the extent of restenosis within the stent, as well as to measure the degree of blood flow, using only MRI and electromagnetic measurement of blood flow.

In German application 197 46 735.0, which was filed as international patent application PCT/DE98/03045, published Apr. 22, 1999 as WO 99/19738, Melzer et al (Melzer, or the 99/19738 publication) disclose an MRI process for represtenting and determining the position of a stent, in which the stent has at least one passive oscillating circuit with an inductor and a capacitor. According to Melzer, the resonance frequency of this circuit substantially corresponds to the resonance frequency of the injected high-frequency radiation from the magnetic resonance system, so that in a locally limited area situated inside or around the stent, a modified signal answer is generated which is represtented with spatial resolution. However, the Melzer solution lacks a suitable integration of an LC circuit within the stent.

Therefore, it is another significant aim of the prestent invention to provide a structure which enhances the properties of the stent itself to allow MRI imaging within the interior of the lumen of the implanted stent.

SUMMARY OF THE INVENTION

The prestent invention resides in a stent configuration and method of use thereof that allows imaging and visualization of the interior of the lumen of the stent after implantation in a body. Interior structures of primary interest and concern consist of body tissue build-up, thrombus formation and the characteristics of blood flow. The imaging is made feasible by a novel stent configuration which includes a tubular scaffolding structure that provides mechanical support for the vessel, duct or channel wall after the stent is deployed at a target site, and additional electrical structure which overlies the mechanically supportive tubular structure. An electrically inductive-capacitive (LC) circuit which is resonant at the magnetic resonant frequency of the MRI energy is formed by a predetermined geometric configuration of an electrically conductive layer overlying the primary mechanically supportive layer of the tubular stent structure or scaffolding of low ferromagnetic property. The two layers are separated from one another by an electrically insulative layer. This structure enables imaging and visualization of the interior of the stent by the non-invasive MRI technique.

In one of its aspects, then, the invention resides in a stent constructed and adapted to be implanted in a vessel, duct or channel of the human body as a scaffolding to maintain patency of the lumen thereof, wherein the stent comprises a mechanically supportive tubular structure composed at least primarily of metal having relatively low ferromagnetic property, and at least one electrically conductive layer overlying at least a portion of the surface of the tubular structure to enhance properties of the stent for MR imaging of the interior of the lumen of the stent when implanted in the body. An electrically insulative layer resides between the surface of the tubular structure and the electrically conductive layer. The tubular structure with overlying electrically conductive layer and electrically insulative layer sandwiched therebetween are arranged in a composite relationship to form an LC circuit at the desired frequency of magnetic resonance. The electrically conductive layer has a geometric formation arranged on the tubular scaffolding of the stent to function as an electrical inductance element and an electrical capacitance element.

In a preferred embodiment of the prestent invention, the tubular scaffolding structure is composed of niobium with a trace amount of zirconium for added strength. The thickness of this structure is preferably up to approximately 100 microns (micrometers, or $\mu m$). The electrically insulative layer is an oxide of the metallic material composing the scaffolding, e.g., a layer of niobium oxide or niobium-zirconium alloy oxide, having a thickness of less than about one $\mu m$, and the electrically conductive layer overlying this insulative layer is preferably composed of niobium, with a thickness of less than about 10 $\mu m$. It is important to avoid electro-galvanic potentials between the scaffolding and conductive structures.

The LC circuit integrated within the stent structure according to the principles of the prestent invention further reduces the already low ferromagnetic properties of the stent and at the magnetic resonant frequency, to enhance visualization of body tissue and tissue growth within the lumen of the implanted stent during the magnetic resonance imaging. The LC circuit also enables measurement of the blood flow through the lumen of stent implanted in a blood vessel.

The LC circuit is alternatively formed as a bird cage or saddle coil pattern.

BRIEF DESCRIPTION OF THE DRAWING

The above and still further aims, objectives, features, aspects and attendant advantages of the prestent invention will become apparent to those skilled in the art from the following detailed description of a best mode prestently contemplated of practicing the invention by reference to certain preferred embodiments and methods of manufacture and use thereof, taken in conjunction with the accompanying drawings, in which.

DETAILED DESCRIPTION OF THE PRESENTLY CONTEMPLATED BEST MODE OF PRACTICING THE INVENTION

Figure 1:
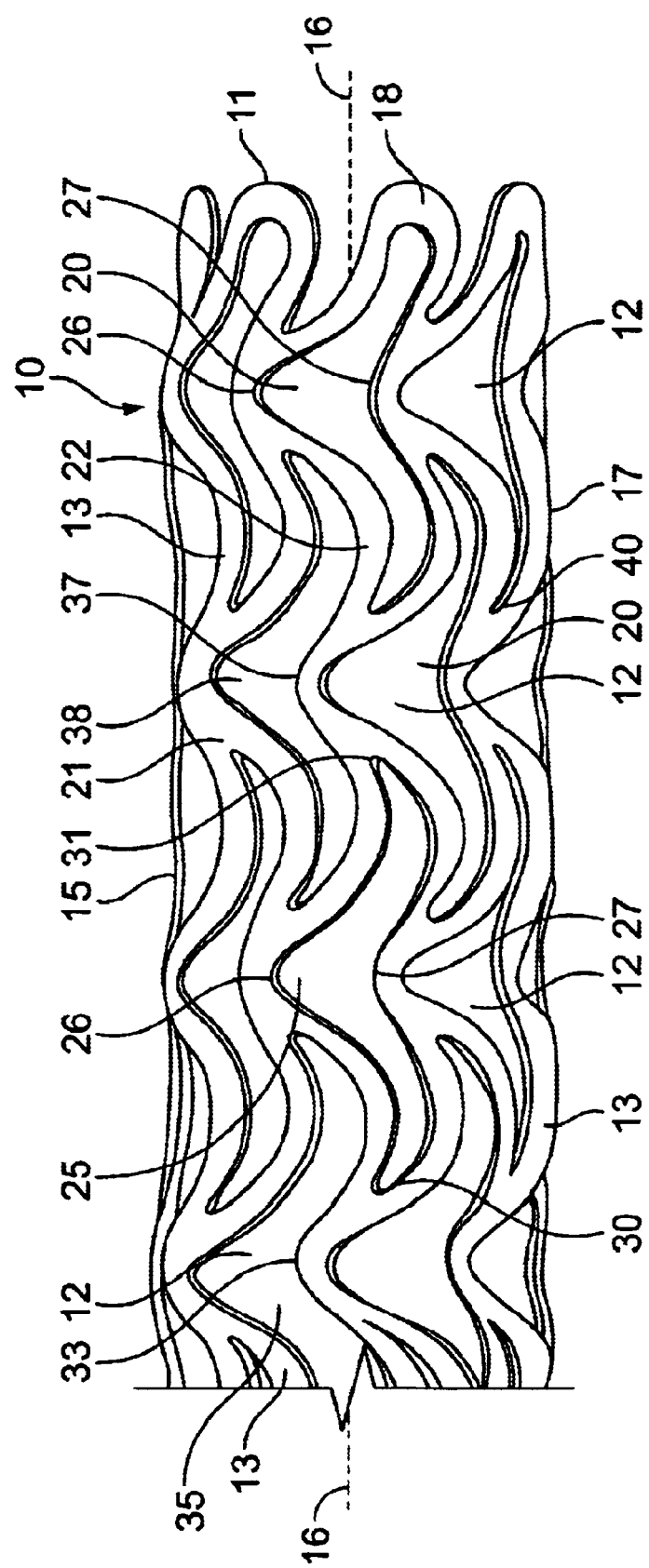
FIG. 1 is a side view of a preferred configuration of the base tubular scaffolding structure of an embodiment of a stent according to the invention.

FIG. 1 is a side view (not to scale) of a preferred configuration of a stent scaffolding structure 10 (albeit this particular configuration is not esstential to the principles of the invention) which may be employed for purposes of the invention. The stent has the form of a hollow tubular self-supporting (i.e., mechanically supportive, when implanted and deployed) structure, preferably composed entirely or principally of niobium. Niobium (Nb) is a lustrous light gray ductile metallic element that resembles tantalum chemically and is frequently used in alloys. Like tantalum, niobium is corrosion resistant and non-ferromagnetic, but is formable, weldable and easier to machine. It has mechanical properties similar to those of steel, and is highly biocompatible which makes it suitable for use in an implant. For enhanced strength and certain other desirable physical characteristics, a trace amount of zirconium is added to the niobium prior to forming the material into a solid tubular shape for processing as the scaffold structure of the stent. The percentage by weight of zirconium in the niobiumzirconium alloy is preferably less than 5%, more preferably less than about 2%, and most preferably less than about 1%, the remainder being niobium. A niobium alloy stent structure is the subject of the aforementioned related co-pending U.S. application Ser. No. 09/663,896. The material is preferably diamagnetic, but a paramagnetic substrate will also suffice.

This stent composition is non-allergenic, has enhanced radiopacity, offers freedom from distortion on MRI, is flexible with suitable elasticity to be plastically deformable, has good mechanical strength (similar to that of steel) to render the stent scaffold resistant to vessel recoil (as invariably occurs after the stent is deployed at a target site in the vessel), all of these characteristics or properties being possessed in a structure sufficiently thin to offer minimal obstruction to flow of blood (or other fluid or material in vessels, ducts, channels or tracts other than the cardiovascular system) by the stent wall. Although a solid tubular structure is preferred (with openings formed through the sidewall to accommodate expansion of the stent during deployment), other known tubular configurations such as wire mesh and coil configurations may alternatively be used The tubular scaffold structure of the stent shown in side view in FIG. 1 has its far side, as viewed in the Figure, omitted to avoid unnecessary clutter and confusion in the depiction. The particular configuration illustrated in the Figure is described in greater detail in co-pending application Ser. No. 08/933,627, which is assigned to the same assignee as this application, but will be described briefly here for the sake of convenience to the reader. Scaffolding structure 10 has a multiplicity of through-holes or openings 12 through its wall (sidewall) 15, which are defined and bounded by a plurality of struts or links 13. The interlaced struts and separating through-holes enable expansion of the stent's diameter for deployment at a target site in a vessel of the human body during implantation of the stent. Holes 12 may be precisely cut out to form the latticework sidewall 15 using a narrow laser beam of a conventional laser following a pre-programmed pattern. The material which is removed to form the openings 12 is discarded. In its configuration shown in FIG. 1, the scaffold structure of the stent is in a slightly opened (i.e., the diameter of the structure is expanded or pre-opened) state.

By way of example and not of limitation, the resulting pattern in the latticework wall 15 constitutes a network of interconnected struts 13 in an optimum orientation predominantly parallel to the longitudinal axis 16 of the tube 11, in which none of the struts is oriented substantially perpendicular (i.e., transverse) to the stent's longitudinal axis 16. In this way, no strut interconnecting any other struts in the latticework is oriented to lie completely in a plane transverse to the longitudinal axis, instead running from one end of the stent to the opposite end. This structure is desirable to provide a very low friction characteristic (or coefficient of friction) of the outer surface 17 of the stent, to ease advancement of stent 10 in a vessel, duct, channel or tract to a target site where the stent is to be deployed. The network or latticework of struts 13 may define a series of longitudinally repeating circumferential rows 20 of openings 12, in which each opening has a shape which resembles the outline of a handlebar moustache, or of a Dutch winged cap, with each opening bounded by alternating links in wavelets of higher and lower crests in successive rows of each circumferential column displaced along the length of the cylindrical element. If FIG. 1 is viewed upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element.

Each pair of struts such as 21, 22 bounding an opening 12 in any given row 25 are in the shape of circumferentially displaced wavelets with adjacent circumferentially aligned higher and lower crests 26, 27, respectively, in which the wavelets intersect one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions will then fit into each other, as the pattern formed by the latticework of struts allows substantial nesting together of the crests and bows, which assures a relatively small circumference of the stent in the crimped condition. Such a stent is highly flexible, and is capable of undergoing bending in an inner arc to a small radius corresponding to radii of particularly tortuous coronary arteries encountered in some individuals, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral or perpendicular orientation relative to the longitudinal axis of the stent. Such lateral orientation of a plurality of the struts enables each fully opened cell to contribute to the firm mechanical support of the scaffolding offered by the stent in its fully deployed condition, to assure a rigid structure which is highly resistant to recoil of the vessel wall following stent deployment. This particular configuration of the stent structure, while highly desirable and preferred in the presently contemplated best mode for practicing the invention, is illustrative only and not a limitation on or esstential to the principles of the prestent invention.

After or just prior to final processing, the stent is preferably pre-opened after fabrication to relieve stresses. Pre-opening produces a stent inner diameter that allows the stent to slide comfortably over the uninflated mounting balloon of the stent delivery system, for ease of crimping the stent onto the balloon. Annealing may be performed after pre-opening by heating the stent structure to an appropriate temperature for a predetermined interval of time.

The niobium/zirconium alloy of which the stent is preferably composed is fabricated in any conventional manner, with a percentage by weight of zirconium amounting from preferably less than about 1%, up to about 5%, and the remainder being niobium. For example, the manufacturing process may be performed by sintering particles or microspheres of the constituent metals under heat and pressure. Instead of zirconium as the trace metal of the primarily niobium alloy, a trace amount (e.g., less than one to three percent) of titanium, tantalum or other metal of similar properties, may be alloyed with the niobium for added strength and other desirable physical characteristics. Other suitable alternative additive materials include those described in U.S. Pat. Nos. 5,472,794 and 5,679,815, for example. The alloy is then formed into tubing and the through holes are provided in its wall by a method such as the previously mentioned laser cutting.

Figure 2:
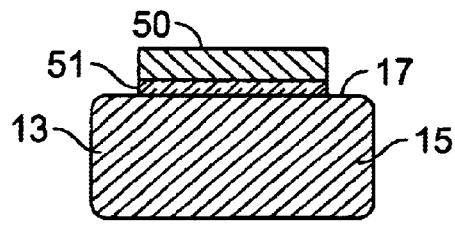
FIG. 2 is a highly magnified cross-sectional view through a strut of the stent configuration of FIG. 1.

According to the invention, two additional layers are adherently super-positioned atop the surface of the scaffolding substrate structure 10 to form a composite structure which provides electrical elements or components that gives the final stent its enhanced properties or characteristics for enabling magnetic resonance imaging of the interior of the lumen of the stent when implanted in the body. FIG. 2 is a cross-sectional view through a strut 13, which is highly magnified for the sake of clarity of the description. The Figure illustrates the principally niobium (pure, or as an alloy with a trace element such as zirconium for strength) substrate 13 of the strut and its overlying layers. The latter comprise an electrically non-conductive, or insulative, layer 51, and an electrically conductive layer 50 formed atop and adherent to the insulative layer. The insulative layer 51 is adherent to the underlying surface 52 of the strut which, itself, is cut or otherwise formed from the wall or sidewall 15 of the original tube from which the stent is fashioned.

The two layers 50 and 51 are confined to preselected portions of the stent substrate surface. Preferably, these layers are applied to or formed upon the outer surface of the stent, rather than to or upon the inner surface along the lumen of the stent. The more practical reason for this is that the manufacturing process is more easily performed using the outer surface location. More importantly, placement at the inner surface of the lumen of the stent would adversely affect the characteristics of blood flow (or flow of other fluid in other ducts) through that lumen when the stent is implanted in a body vessel. The two layers—electrically conductive layer 50 and insulative layer 51—contribute little or nothing to the mechanical properties of the stent, but provide important features in magnetic resonance imaging of the implant region.

The physics and basics of magnetic resonance imaging (MRI) are well known, so only a summary will suffice here. An external magnetic field induces a spin in the atomic nuclei, which is a function of the direction, strength and change in the externally applied magnetic field. The spin of the atomic nuclei consists of several signals, which can be separated and described by different relaxation times t1 and t2. Certain mathematical methods are used to recover or receive a signal outside the body which is proportional to the structure of the material, especially of the tissue, in the human body subjected to the MRI procedure.

These mathematical methods consider the total magnetic resonance frequency, the total magnetic energy, and the gradient between the different relaxation times, and, together with the use of contrast dyes which change the paramagnetic properties of the tissue, enable an image to be created according to the external application of the magnetic resonance energy. The imaging creates three-dimensional pictures of not only external structures of the body, but of virtually any region within the body subjected to the MRI energy. An obstacle for creation of a complete and accurate 3-D picture is any metallic implant in the patient's body, since this operates to produce a distortion of the MRI imaging, depending in part on the implant's ferromagnetic properties.

The externally applied magnetic resonance imaging energy may be amplified, and a spatial resolution achieved, by use of an inductive-capacitive circuit—an LC circuit—at the magnetic resonance frequency, as pointed out in the aforementioned 99/19738 publication.

In the device and method of the invention, a structure which forms the simple electrical circuitry of a spool to achieve amplification of the externally applied magnetic energy of the MRI apparatus is achieved by the conductive and insulative layers 50 and 51, respectively, provided on the scaffolding structure of stent 10, so that the LC circuit is integrated into the stent itself. The sidewall 15 of stent 10, and hence, the strut wall 13 itself, has a thickness in a range of 100 microns or less in the case of a coronary stent, for example. The typical coronary artery in which a stent is implanted has a diameter in a range of from 2 to 5 millimeters (mm). A stent which is to be implanted in vessels of larger diameter may and typically would have a thicker wall.

The electrical insulation layer 51 is preferably an oxide of the metal that forms the stent. In the preferred embodiment, the stent scaffolding structure or substrate is composed of pure niobium or an alloy of niobium with a trace of a strengthening element such as zirconium; hence, the layer 51 is preferably niobium oxide or niobium-zirconium oxide.

Electrically conductive layer 50 overlying the insulative layer is preferably composed of niobium, has a thickness considerably less than the thickness of the stent wall, and a width which preferably is less than the width of the underlying strut 13. In a preferred exemplary embodiment, the electrically conductive layer 50 has a thickness less than 10 microns, and a width from about 80 to about 100 microns, which in any event is not greater than the width of the strut.

Figure 4:
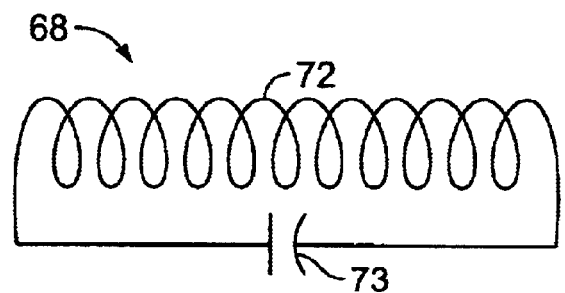
FIG. 4 is a schematic illustration of the LC electrical circuit.
Figure 3:
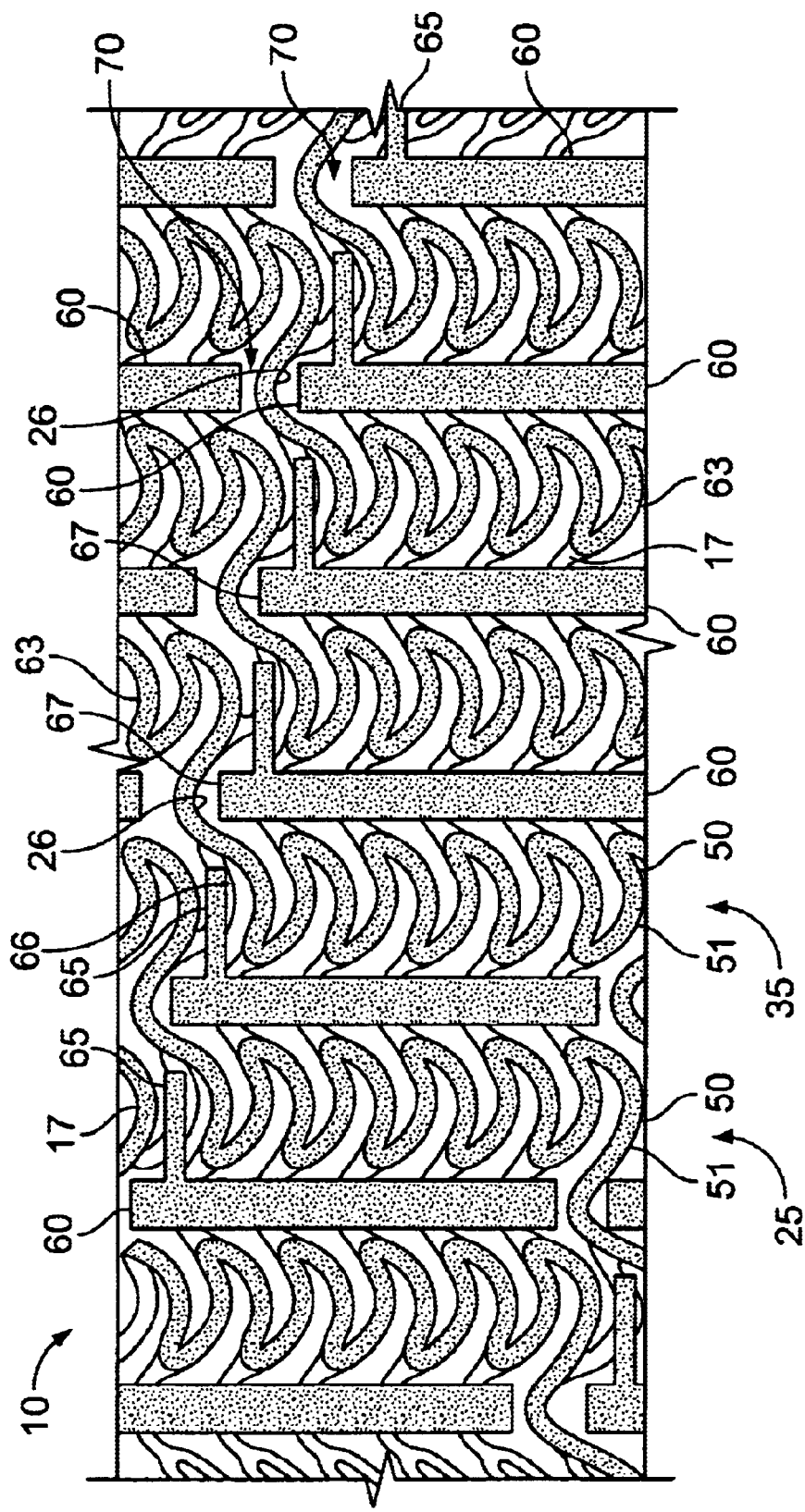
FIG. 3 is a development side view of a portion of the stent which illustrates physical formation of the LC circuit on the surface of the stent substrate structure.

FIG. 3 is a development side view of a portion of the stent which illustrates physical formation of the LC circuit on the surface of the stent substrate, and FIG. 4 is a schematic illustration of the LC electrical circuit 68. Unlike the prior art, the LC circuit is integrated within the stent itself. The physical structure of the LC circuit is determined or calculated to be resonant at the magnetic resonance frequency of the MRI energy. This will allow the MRI image to depict the region within the lumen of the stent, as well as the region external to the stent which would ordinarily be viewable by MRI, without significant distortion.

The black bars 60 (transverse to the longitudinal axis of the stent) in FIG. 3 represent temporary mask locations over the outer surface 17 of the stent (as opposed to the inner surface which constitutes the surface of the lumen of the stent). As shown in this Figure, the coil portions 63 are formed in a predetermined pattern on outer surface 17. This is achieved by first depositing (or otherwise creating, such as by heating the stent in an atmosphere of oxygen to form an oxide of the underlying metal, e.g., niobium, in other than surface masked regions) the thin electrically insulative layer 51 (such as niobium oxide) on the external surface 17 of adjacent struts 13 in a circumferential row 25, in a continuous lineal pattern. Longitudinal extensions 65 of mask bars 60 indicate struts 66 which are to be left free of an insulative layer 51 and where, instead, that layer is to extend lineally by jumping to struts in the next adjacent circumferential row 35 above (or below, depending on the vantage point) the relevant mask extension 65. The corresponding ends 67 of longitudinally adjacent bars 60 are displaced or offset to terminate below (or above, depending on vantage point) the higher crest 26 of wavelets in the adjacent rows to leave a one-crest gap 70 between confronting ends of circumferentially adjacent bars 60. This leaves a longitudinally stepped gap at which the jump in lineal application of insulative layer 51 is to be made. In effect, the mask creates a map for application of this strip. The previously described electrically conductive layer 50 is then formed by application (e.g., by deposition) directly atop and adherent to insulative layer 51.

With two circumferentially aligned mask bars 60 in each row of struts, this process results in two sub-coils which are then connected at adjacent ends to form a single continuous coil 72 (FIG. 4). The opposing ends of this overall coil 72 are effectively coupled together through a capacitance element 73 which is created by the close separation between the two sub-coils in application pattern of the conductive layer 50 on the stent. As a result, the LC circuit 68 is formed as an integral part of stent 10. The geometry of the LC circuit including the length of the coil and the capacitance produced by the spacing between the adjacent sub-coils is predetermined to achieve the desired magnetic resonance frequency.

Figure 5:
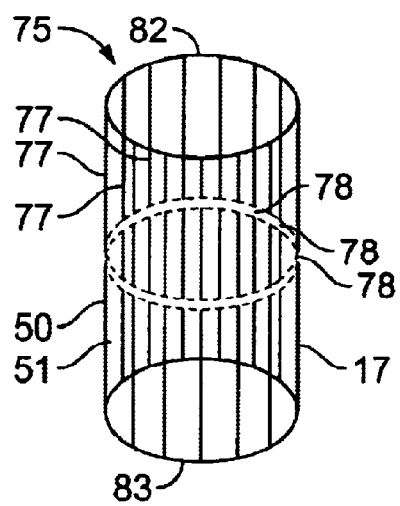
FIG. 5 is a diagram illustrating an LC circuit formed using the principle of a bird cage.

As an alternative to this technique or method of forming LC circuit 68, the principle of a bird cage may be used, as illustrated in FIG. 5. The bird cage 75 has longitudinal elements 77, which are formed by applying strips of a conductive layer 50 overlying strips of an insulative layer 51 atop the outer surface 17 of a series of longitudinally aligned and interconnected struts from end to end of the stent, as described above, except for a break or interruption 78 at a central point of each longitudinal element. At each end 79, 80 of the stent the corresponding ends of these longitudinal elements 77 are connected together by a respective transverse circumferential connecting strip 82,83 of the conductive layer overlying a similarly situated insulative layer atop the outer surface 17 of the stent. The result is an integral LC circuit as in FIG. 4, having a magnetic resonance frequency determined according its geometry.

Figure 6:
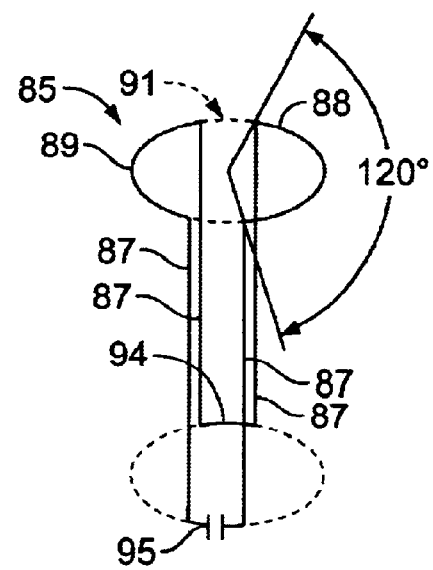
FIG. 6 is a diagram illustrating an LC circuit using a saddle coil principle.

Another alternative form that provides LC circuit 68 is shown as a so-called saddle coil 85 in FIG. 6. In this example, four conductive longitudinal elements 87 are created on four series of longitudinally aligned and interconnected struts from end to end of the stent, as described above but without central interruption. Two sets of two each of the elements 87 residing at 120 degree separation are connected together at one end of the stent by partial circumferential end conductive elements 88, 89, respectively. Each of these two sets is separated at opposite sides circumferentially of the stent by 60 degree gaps 91, 92. At the other end of the stent, two of the adjacent conductive elements 87 residing at 60 degree separation (e.g., separated by gap 91) in one pair of opposite ones of the two sets are connected together by partial circumferential end conductive element 94. The spacing between the longitudinal elements of the two sets creates an effective capacitance 95 between elements 87 of the other pair of opposite ones of the two sets.

Fabricating the electrically conductive and insulative layers atop the scaffolding or substrate mechanical structure may be performed as described above. To avoid galvanic potentials, it is preferable that the mechanical structure and the electrically conductive structure should consist of materials of similar electro-galvanic potential, and, in the extreme, composed of materials from the same metallic group. A mask (e.g., a traditional mask including photoresist or otherwise) may be applied to the substrate structure, the insulative (e.g., oxide) layer and the overlying conductive layer may be formed by sputtering or vapor deposition or other known techniques for applying a metal or other material to a preexisting structure under vacuum and electrical high energy fields. Alternatively, the entire outer surface of the stent scaffolding structure may be covered by layers of insulation (oxide) and conductive material, after which selected portions may be removed, as by known laser removal techniques.

The geometric structures are created and defined by the use of an appropriate mask. The resonant frequency of the inductive-capacitive circuit structure may be adjusted as desired according to the geometric configuration of the outer conductive layer atop the insulative layer.

Although a best mode of practicing the invention has been disclosed by reference to certain preferred embodiments and methods, it will be apparent to those skilled in the art from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A stent adapted to be implanted in a duct of a human body to maintain an open lumen at the implant site, and to allow viewing body properties outside and within the implanted stent by magnetic resonance imaging (MRI) energy applied external to the body, said stent comprising a metal scaffold, and an electrical circuit resonant at the resonance frequency of said MRI energy integral with said scaffold.

2. A stent adapted to be implanted in a duct of a human body to maintain an open lumen at the implant site, said stent comprising a tubular scaffold of low ferromagnetic metal, and an inductance-cpacitance (LC) circuit integral with said scaffold, said LC circuit being geometrically structured in combination with said scaffold to be resonant at the resonance frequency of magnetic resonance imaging (MRI) energy to be applied to said body to enable MRI viewing of body tissue and fluid within the lumen of the stent when implanted and subjected to said MRI energy.

3. The stent of claim 2, wherein said metal is at least primarily niobium.

4. The stent of claim 3, wherein said LC circuit is composed of successive layers of an oxide of said metal overlying said scaffold and the same composition as said metal overlying said oxide layer.

5. A stent constructed and adapted to be implanted in a vessel, duct or channel of the human body to maintain patency of the lumen thereof and to allow substantially distortion-free magnetic resonance imaging (MRI) of the interior of the stent when implanted and subjected to MRI energy, said stent comprising a tubular scaffolding structure composed at least primarily of metal having sufficiently low ferromagnetic property to avoid material distortion of the magnetic resonance field, at least one electrically conductive layer overlying at least a portion of the surface of said scaffolding structure to enhance properties of the stent for magnetic resonance imagine (MRI) of the interior of the stent when implanted, and an electrically insulative layer residing between said at least a portion of the surface of said scaffolding structure and said at least one electrically conductive layer, wherein said electrically insulative layer is formed from an oxide of the metal of said scaffolding structure.

6. The stent of claim 5, wherein said tubular scaffolding structure is composed at least primarily of niobium and said electrically insulative layer is composed of niobium oxide.

7. The stent of claim 5, wherein said tubular scaffolding structure is composed at least primarily of niobium zirconium alloy and said electrically insulative layer is composed of niobium zirconium oxide.

8. The stent of claim 5, wherein said scaffolding structure and said electrically conductive and insulative layers are geometrically arranged in a composite relationship to form an inductance capacitance (LC) circuit having a resonant frequency to enable visualization of body tissue and tissue growth within the lumen of the implanted stent by MRI.

9. The stent of claim 8, wherein the resonant frequency of said LC circuit is made by said geometrical arrangement to be equivalent to the resonance frequency of the MRI energy to which the stent is to be subjected in the body.

10. The stent of claim 8, wherein said LC circuit is formed to enable measurement of blood flow through the lumen of said stent when implanted in a blood vessel of the body.

11. The stent of claim 8, wherein said LC circuit is formed as a bird cage element.

12. The stent of claim 8, wherein said LC circuit is formed as a saddle coil element.

13. A stent constructed and adapted to be implanted in a vessel, duct or channel of the human body to maintain patency of the lumen thereof and to allow substantially distortion-free magnetic resonance imaging (MRI) of the interior of the stent when implanted and subjected to MRI energy, said stent comprising a tubular scaffolding structure composed at least primarily of metal having sufficiently low ferromagnetic property to avoid material distortion of the magnetic resonance field, at least one electrically conductive layer overlying at least a portion of the surface of said scaffolding structure, and an electrically insulative layer residing between said at least a portion of the surface of said scaffolding structure and said at least one electrically conductive layer, said scaffolding structure and said conductive and insulative layers being geometrically arranged in a composite relationship to form an inductance capacitance (LC) circuit integrated within the stent for resonance at the magnetic resonance frequency of the MRI energy so as to enable the MRI image to depict the region within and external to the stent without material distortion.

14. The stent of claim 13, wherein said at least one electrically conductive layer has a geometric formation arranged to function as an electrical inductance element.

15. The stent of claim 13, wherein said at least one electrically conductive layer has a geometric formation arranged to function as an electrical capacitance element.

16. The stent of claim 13, wherein said at least one electrically conductive layer is structured to function electrically as both an inductance element and a capacitance element.

17. The stent of claim 13, wherein said at least one electrically conductive layer has a thickness of less than about 10 $\mu$m.

18. The stent of claim 13, wherein said tubular scaffolding structure has a thickness considerably greater than the thickness of said at least one electrically conductive layer.

19. The stent of claim 13, wherein said at least one electrically conductive layer has a thickness of less than about 10 $\mu$m, and said electrically insulative layer has a thickness of less than about 1 $\mu$m.

20. The stent of claim 3, wherein said at least one electrically conductive layer is spaced apart from the surface of said tubular structure by the thickness of said electrically insulative layer.

* * * * *